US006936625B2

(12) United States Patent
Moon et al.

(10) Patent No.: US 6,936,625 B2
(45) Date of Patent: Aug. 30, 2005

(54) AMLODIPINE CAMSYLATE AND METHOD FOR PREPARING THEREOF

(75) Inventors: Young-Ho Moon, Suwon-si (KR); Nam-Du Kim, Osan-si (KR); Kyung-Ik Lee, Incheon (KR); Gwan-Sun Lee, Seoul (KR); Jong-Soo Woo, Suwon-si (KR)

(73) Assignee: Hanmi Pharm. Co., Ltd. (KR)

( * ) Notice: Subject to any disclaimer, the term of this patent is extended or adjusted under 35 U.S.C. 154(b) by 136 days.

(21) Appl. No.: 10/473,479

(22) PCT Filed: Mar. 28, 2002

(86) PCT No.: PCT/KR02/00543

§ 371 (c)(1), (2), (4) Date: Sep. 26, 2003

(87) PCT Pub. No.: WO02/079158

PCT Pub. Date: Oct. 10, 2002

(65) Prior Publication Data

US 2004/0116478 A1 Jun. 17, 2004

(30) Foreign Application Priority Data

Mar. 29, 2001 (KR) ........................................ 2001-16514

(51) Int. Cl.[7] ................... A61K 31/4418; C07D 213/80
(52) U.S. Cl. ........................................ 514/356; 546/321
(58) Field of Search .......................... 546/321; 514/356

(56) References Cited

U.S. PATENT DOCUMENTS

| 4,572,909 A | 2/1986 | Campbell et al. |
| 6,057,344 A | 5/2000 | Young |
| 6,518,288 B2 * | 2/2003 | Lemmens et al. .......... 514/356 |

FOREIGN PATENT DOCUMENTS

| KR | 1995-7228 | 7/1995 |
| KR | 000063287 A | 6/2000 |

* cited by examiner

Primary Examiner—Patricia L. Morris
(74) Attorney, Agent, or Firm—Anderson Kill & Olick, PC

(57) ABSTRACT

Amlodipine camsylate of the present invention is a crystalline salt of amlodipine suitable for pharmaceutical formulation, which is prepared by using low toxic camphor sulfonic acid to meet required pharmaceutical properties for treating cardiovascular diseases.

8 Claims, 3 Drawing Sheets

AMLODIPINE CAMSYLATE AND METHOD FOR PREPARING THEREOF

FIELD OF THE INVENTION

The present invention relates to amlodipine camsylate of formula (1) and a method for preparing thereof.

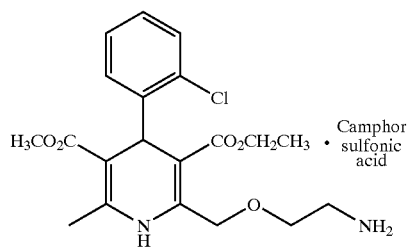

(1)

BACKGROUND OF THE INVENTION

Amlodipine, a generic name for the compound of formula (2), 3-ethyl-5-methyl-2-(2-aminoethoxy-methyl)-4-(2-chlorophenyl)-6-methyl-1,4-dihydro-3,5,-pyridine dicarboxylate, is a long-term calcium-channel blocker useful for treating cadiovacular diseases such as stenocardia, hypertension and congestive cardioplegic.

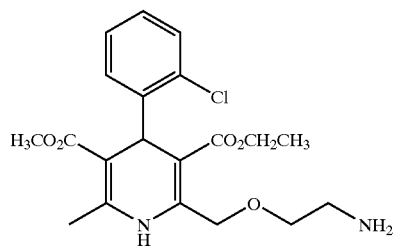

(2)

European Patent Publication No. 89167 discloses various different types of pharmaceutically acceptable salts of amlodipine. A pharmaceutically acceptable salt is made by adding a pharmaceutically acceptable acid to form a non-toxic salt of amlodipine acid type, and examples thereof include hydrochloride, hydrobromide, sulfate, phosphate or acidic phosphate, acetate, maleate, fumarate, lactate, tartarate, citrate and gluconate. Among these salts, maleate is most preferable.

Amlodipine in the form of a free base is useful for pharmaceutical use. However, because amorphous amlodipine shows a low stability, it is preferable to administer in the form of a salt of a pharmaceutically acceptable acid.

Korean Patent Publication No. 95-6710 suggests that a pharmaceutically acceptable salt must meet four physico-chemical requirements: high solubility, good stability, non-hygroscopicity and processibility for tablet formulation.

Most amlodipine salts are amorphous and it is difficult to prepare purely them. Further, an acid-added salt of amlodipine that meets all the above requirements is yet to be developed. For example, it has been found that even amlodipine maleate, which is proposed as the most preferable pharmaceutical form of amlodipine, has a relatively high solubility in water, but degrades in a solution within several weeks.

Korean Patent Publication No. 95-7228 discloses that amlodipine benzenesulfonate (hereinafter, "amlodipine besylate") shows a high solubility and good stability, and has suitable properties for preparing a pharmaceutical formulation. However, amlodipine besylate is derived from toxic benzene sulfonic acid, and therefore, there exists a safety issue.

The present inventors have endeavored to develop a novel crystalline amlodipine that satisfies all the require properties.

SUMMARY OF THE INVENTION

Accordingly, it is a primary object of the present invention to provide a novel crystalline salt of amlodipine which is low toxic and has pharmaceutically acceptable properties.

In accordance with one aspect of the present invention, there is provided a method for preparing a crystalline salt of amlodipine using relatively low toxic camphor sulfonic acid than benzenesulfonic acid.

In accordance with still another aspect of the present invention, there is provided amlodipine camsylate having the structure of formula (1) which is prepared by the inventive method.

In accordance with further aspect of the present invention, there is provided a pharmaceutical composition for treating cadiovacular diseases comprising the amlodipine camsylate as an effective ingredient.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

The present invention provides a method for preparing a crystalline salt of amlodipine using low toxic camphor sulfonic acid.

In detail, the method of the present invention comprises the steps of:

1) dissolving amlodipine of formula (2) in an organic solvent;
2) adding a camphor sulfonic acid solution in an organic solvent to the amlodipine solution and agitating the mixture for a period sufficient to form a solid;
3) filtering, washing and drying the solid.

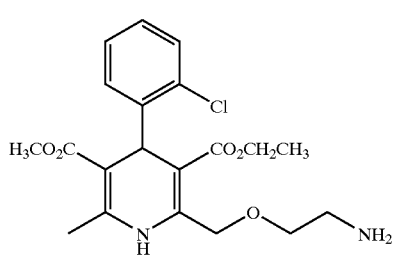

(2)

A crystalline salt of amlodipine in accordance with the present invention may be prepared by adding an acid into the amlodipine solution or adding an acid into the reaction mixture for preparing amlodipine.

It is preferable to use amlodipine of step 1) in the concentration of 3 to 60 weight % to efficiently promote a crystallization, more preferably 10 to 30 weight %.

Camphor sulfonic acid which may be employed in step 2) includes, but are not limited to, (1S)-(+)-10-camphor sulfonic acid of formula (3), (1R)-(−)-10-camphor sulfonic acid of formula (4) and racemic 10-camphor sulfonic acid. It is preferable to use camphor sulfonic acid in the amount of 0.1 to 5.0 equivalent based on the amount of amlodipine, more preferably 1.0 to 1.3 equivalent.

An organic solvent used in step 1) or 2) includes methanol, ethanol, isopropanol and acetonitrile.

The solid in step 2) is preferably formed at −10 to 50° C., more preferably 0 to 25° C.

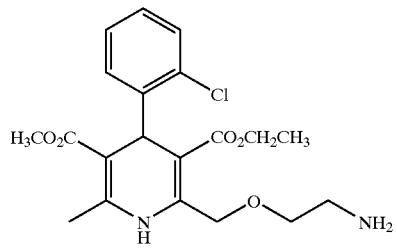

(2)

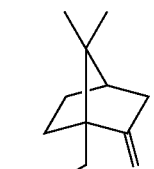

(3)

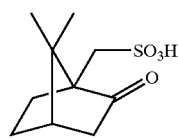

(4)

Further, the present invention provides amlodipine camsylate prepared by the inventive method which is low toxic and has pharmaceutically acceptable properties.

Figure 1:
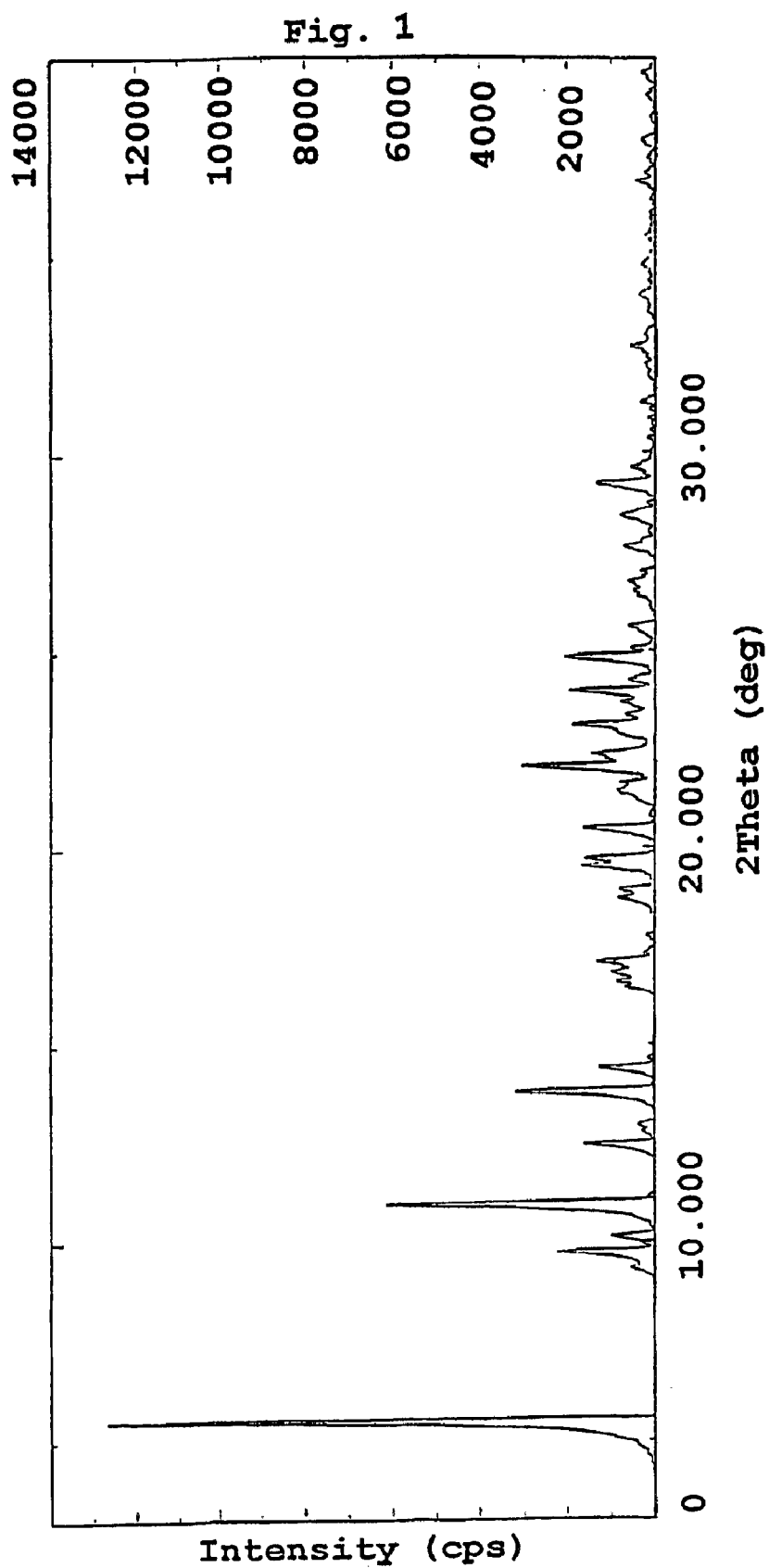
FIG. 1: an X-ray diffraction scan of amlodipine camsylate of the present invention.
Figure 2:
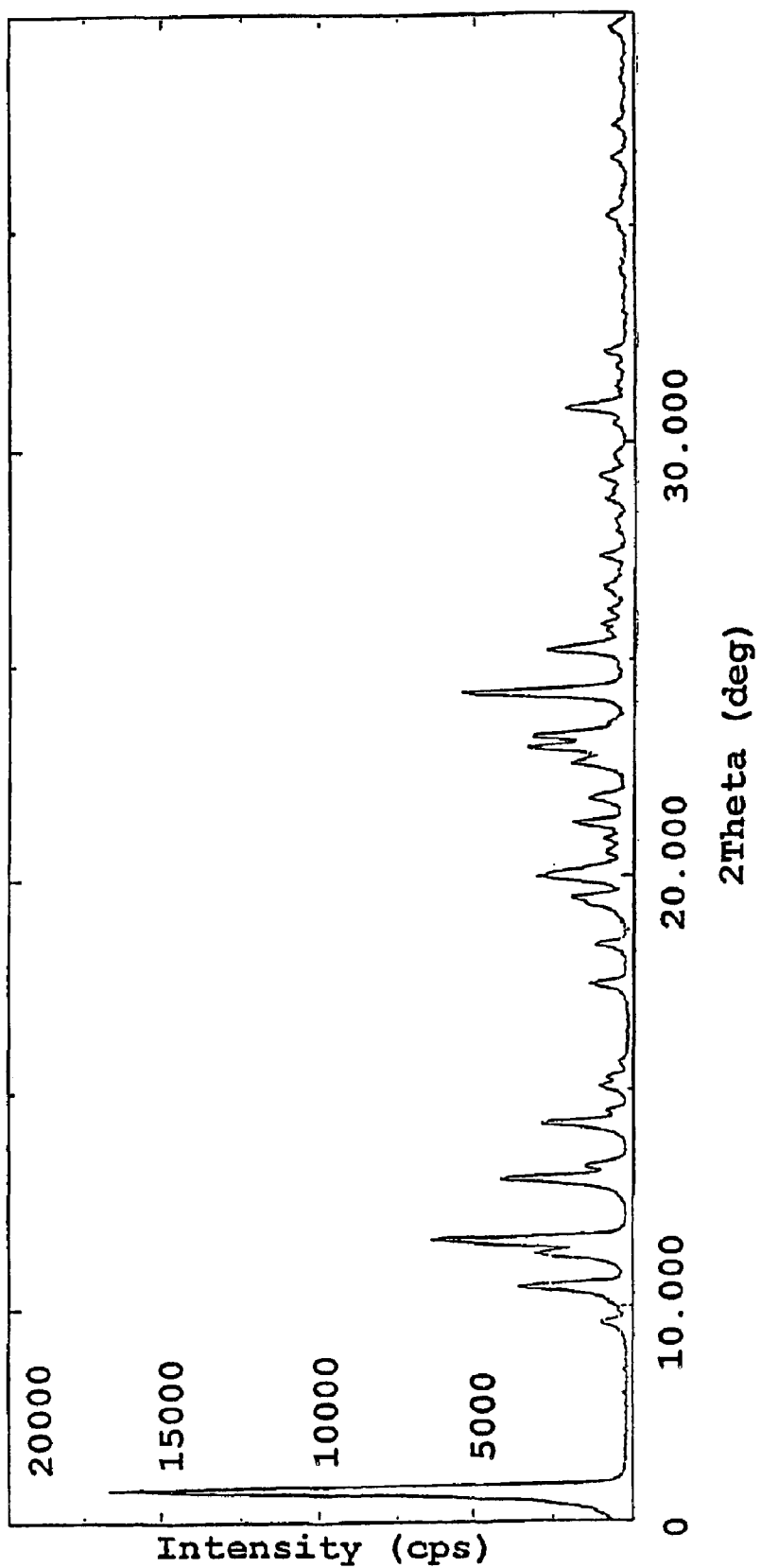
FIG. 2: an X-ray diffraction scan of amlodipine besylate.

It has been proved that the inventive crystalline salt of amlodipine, amlodipine camsylate, has a different crystal form from that of amorphous compound or amlodipine besylate via X-ray diffraction scan (see FIGS. 1 and 2), and has a structure of formula (1) via NMR analysis.

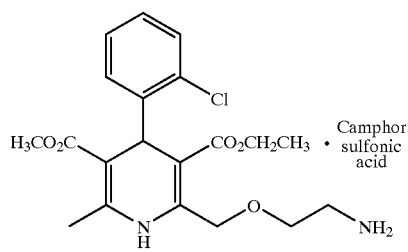

(1)

It has been well-known that amlodipine besylate is the most suitable for a pharmaceutical formulation, but has a problem with stability due to the use of toxic benzene sulfonic acid. To solve this problem, the present invention uses relatively low toxic camphor sulfonic acid than benzenesulfonic acid.

A toxicity of camphor sulfonic acid is compared with that of benzene sulfonic acid according to Registry of Toxic Effects of Chemical Substances (RTECS) data, and a comparative result is described in Table 1.

TABLE 1

| Substance | Administration route | Subject animal | Dose | Reference |
|---|---|---|---|---|
| Benzene sulfonic acid | Oral | Rat | $LD_{50}$ 890 µl/kg | AIHAAP 23,95,1962 |
| | Cutaneous | Cat | $LD_{LO}$ 10 g/kg | JPETAB 84,358,1945 |
| | Oral | Wildbirds | $LD_{50}$ 75 mg/kg | TXAPA9 21,315,1972 |
| (1S)-(+)-10-Camphor sulfonic acid | Subcutaneous | Mouse | $LD_{50}$ 2502 mg/kg | PHARAT 1,150,1946 |
| (±)-10-Camphor sulfonic aicd | Oral | Quail | $LD_{50}$ > 316 mg/kg | EESADV 6,149,1982 |

$LD_{50}$: 50% fetal dose,
$LD_{LO}$: the minimum fetal dose

As illustrated in Table 1, since it is impossible to compare $LD_{50}$ value about same species between them, it is difficult to directly compare the toxicity of camphor sulfonic acid with that of benzene sulfonic acid, however, it can be confirmed that camphor sulfonic acid used in the present invention shows lower toxicity than benzene sulfonic acid.

Furthermore, the present invention provides a pharmaceutical composition for treating a cadiovacular disease comprising the inventive amlodipine camsylate as an effective ingredient and pharmaceutically acceptable excipients, carriers or diluents.

A pharmaceutical composition may be prepared in accordance with any of the conventional procedures. In preparing the composition, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil. The compositions may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of amlodipine camsylate may range from about 1.0 to 10.0 mg/kg body weight, preferably 5.0 to 8.0 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The following Examples and Test Examples are given for the purpose of illustration only, and are not intended to limit the scope of the invention.

EXAMPLE 1

Preparation of Amlodipine Camsylate 1

12.25 g (0.03 mol) of amlodipine (Hanmi Pharm. Co. Ltd.) was dissolved in 50 ml of methanol, cooled to 10° C., and a solution of 7.8 g (0.336 mol) of (1S)-(+)-10-camphor sulfonic acid (Aldrich) in 19.5 ml of methanol was gradually added thereto. After the reaction mixture was stirred at room temperature for 2 hours, the solid formed compound was filtered, washed with 25 ml of methanol, and dried to obtain 16.7 g (yield: 86.8%) of the title compound in the form of a white crystal.

m.p: 198° C.~202° C.

$^1$H-NMR (300 MHz, DMSO-d$_6$)δ (ppm): 8.42(s, 1H), 7.82(br, 3H), 7.35~7.13(m, 4H, ArH), 5.30(s, 1H), 4.73~4.55(d.d., 2H), 3.96(q, 2H), 3.65(m, 2H), 3.50(s, 3H), 3.34(s, 2H), 3.08(m, 2H), 2.90~2.35(d.d., 2H), 2.70(m, 1H), 2.31(s, 3H), 2.28~2.21(m, 1H), 1.95~1.77(m, 3H), 1.27(m, 2H), 1.26(t, 3H), 1.05(s, 3H), 0.74(s, 3H)

EXAMPLE 2

Preparation of Amlodipine Camsylate 2

12.25 g (0.03 mol) of amlodipine was dissolved in 50 ml of methanol, cooled to 10° C., and a solution of 7.8 g (0.336 mol) of (1R)-(−)-10-camphor sulfonic acid (Aldrich) in 19.5 mg of methanol was gradually added thereto. 15.4 g (yield: 80.0%) of the title compound in the form of a white crystal was obtained by using the same method described in Example 1.

m.p: 198° C.~204° C.

$^1$H-NMR (300 MHz, DMSO-d$_6$)δ (ppm): 8.42(s, 1H), 7.82(br, 3H), 7.35~7.13(m, 4H, ArH), 5.30(s, 1H), 4.73~4.55(d.d., 2H), 3.96(q, 2H), 3.65(m, 2H), 3.50(s, 3H), 3.34(s, 2H), 3.08(m, 2H), 2.90~2.35(d.d., 2H), 2.70(m, 1H), 2.31(s, 3H), 2.28~2.21(m, 1H), 1.95~1.77(m, 3H), 1.27(m, 2H), 1.26(t, 3H), 1.05(s, 0.3H), 0.74(s, 3H)

EXAMPLE 3

Preparation of Amlodipine Camsylate 3

12.25 g (0.03 mol) of amlodipine was dissolved in 50 ml of methanol, cooled to 10° C., and a solution of 7.8 g (0.336 mol) of (±)-10-camphor sulfonic acid (Aldrich) in 19.5 ml of methanol was gradually added thereto. 16.0 g (yield: 83.2%) of the title compound in the form of a white crystal was obtained by using the same method described in Example 1.

m.p: 198° C.~204° C.

$^1$H-NMR (300 MHz, DMSO-d$_6$)δ (ppm): 8.42(s, 1H), 7.82(br, 3H), 7.35~7.13(m, 4H, ArH), 5.30(s, 1H), 4.73~4.55(d.d., 2H), 3.96(q, 2H), 3.65(m, 2H), 3.50(s, 3H), 3.34(s, 2H), 3.08(m, 2H), 2.90~2.35(d.d., 2H), 2.70(m, 1H), 2.31(s, 3H), 2.28~2.21(m, 1H), 1.95~1.77(m, 3H), 1.27(m, 2H), 1.26(t, 3H), 1.05(s, 3H), 0.74(s, 3H)

EXPERIMENTAL EXAMPLE 1

Solubility Test

An amlodipine salt preferably has a solubility in water of more 1 mg/ml at pH 1 to 7.5, particularly at the blood pH value of 7.4. Accordingly, the solubility and saturation pH of each of the amlodipine camsylates prepared in Examples 1 and 2 were measured and compared with those of amlodipine besylate (Korean Patent Publication No. 95-7228). The measurement was performed according to the procedure described in the Korean Pharmacopoeia (Korean Ministry of Health and Welfare, General principle of medical supplies, Vol. 1, Clause 29, the 7$^{th}$ revision) which comprises the steps of dissolving each compound in distilled water to saturation, analyzing the saturated solution with liquid chromatography, and measuring the dissolved amount of each compound based on the amount of amlodipine.

TABLE 2

| Salt | Solubility (mg/ml) | Saturation pH |
| --- | --- | --- |
| Amlodipine besylate | 1.398 | 6.2 |
| Amlodipine camsylate of Example 1 (S) | 1.225 | 6.0 |
| Amlodipine camsylate of Example 2 (R) | 1.250 | 6.2 |

As illustrated in Table 2, the saturation pH of the inventive amlodipine camsylate was similar to that of amlodipine besylate, but its solubility was slightly lower than that of amlodipine besylate, possibly due to the molecular weight difference between amlodipine camsylate (M.W=641.18) and amlodipine besylate (M.W=559.06).

EXPERIMENTAL EXAMPLE 2

Stability Test

The time-dependent stability of the inventive amlodipine camsylate prepared in Examples 1 and 2 was measured and compared with that of amlodipine besylate. Specifically, each compound was stored at 55° C., a relative humidity of about 50%, and after 1, 2, 3 and 4 weeks, the remaining amount of active amlodipine was determined with a liquid chromatography.

TABLE 3

| Salt | Initial | 1 week | 2 weeks | 3 weeks | 4 weeks |
| --- | --- | --- | --- | --- | --- |
| Amlodipine besylate | 1 | 0.992 | 0.996 | 0.993 | 0.993 |
| Amlodipine camsylate of Example 1 (S) | 1 | 1 | 0.998 | 1 | 1 |
| Amlodipine camsylate of Example 2 (R) | 1 | 1 | 1 | 1.002 | 1 |

As shown in Table 3, while amlodipine besylate underwent slight but significant degradation after 1 week, the inventive amlodipine camsylate was stable during the 4 weeks period. Therefore, the inventive amlodipine camsylate is more stable than amlodipine besylate.

EXPERIMENTAL EXAMPLE 3

Non-Hydroscopicity Test

When a solid form of a drug is to be formulated, it is important that the drug is not hygroscopic. Accordingly, the hygroscopicity of the inventive amlodipine camsylate was measured and compared with that of amlodipine besylate.

Each compound was exposed to two conditions: 37° C. under 75% relative humidity for 24 hours (condition 1) and 30° C. under 95% relative humidity for 3 days (condition 2), and then, the moisture content of each compound was measured according to the method described in Korean Patent Publication No. 1995-7228.

TABLE 4

| Salt | Initial moisture (%) | Condition 1 (%) | Condition 2 (%) |
|---|---|---|---|
| Amlodipine besylate | 0.05 | 0.05 | 0.15 |
| Amlodipine camsylate of Example 1 (S) | 0.05 | 0.05 | 0.15 |
| Amlodipine camsylate of Example 2 (R) | 0.05 | 0.05 | 0.15 |

The result in Table 4 shows that neither the inventive amlodipine camsylate nor amlodipine besylate was hygroscopic.

EXPERIMENTAL EXAMPLE 4

Comparative Adhesion Test

The adhesive property of the inventive amlodipine camsylate was measured and compared with that of amlodipine besylate as follows.

Each compound was subjected to tableting according to the procedure described in Korean Patent Publication No. 95-7228, and the compound remained adhered to the tablet punch was extracted with methanol at various tableting amounts and the amount thereof was measured with a spectrometer. A mean value of multiple measurements was determined from the slopes of the linear lines in FIG. 3.

TABLE 5

| | Absorbed amount of tablet (µg) | | | | | |
|---|---|---|---|---|---|---|
| Tablet | Amlodipine besylate | | Amlodipine camsylate | | Camsylate/ besylate | |
| amount | AVG. | S.D | AVG. | S.D | AVG. | S.D |
| 50 | 32.9 | 5.6 | 33.0 | 8.2 | 1.00 | 0.08 |
| 100 | 60.6 | 2.5 | 60.6 | 9.1 | 0.99 | 0.11 |
| 150 | 102.7 | 15.7 | 101.1 | 14.6 | 0.99 | 0.01 |
| 220 | 183.8 | 1.1 | 177.1 | 2.1 | 0.96 | 0.01 |
| 250 | 235.1 | 5.3 | 234.8 | 13.3 | 1.00 | 0.03 |
| 300 | 242.7 | 2.6 | 235.4 | 1.4 | 0.97 | 0.02 |

Figure 3:
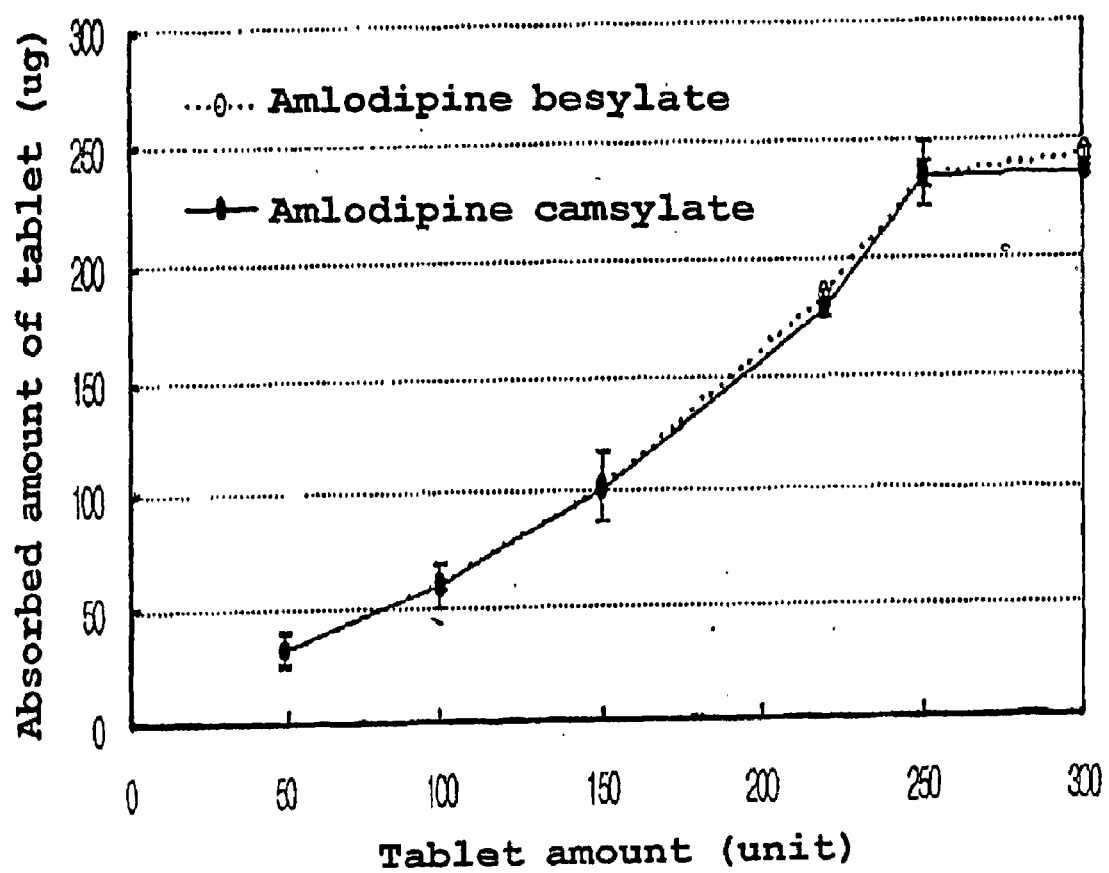
FIG. 3: adhesive properties of the inventive amlodipine camsylate and amlodipine besylate.

As can be seen in Table 5, the inventive amlodipine camsylate and amlodipine besylate are equally in terms of adhesive inhibitory property (FIG. 3).

While the invention has been described with respect to the above specific embodiments, it should be recognized that various modifications and changes may be made to the invention by those skilled in the art which also fall within the scope of the invention as defined by the appended claims.

What is claimed is:

1. Amlodipine camsylate having the structure of formula (1):

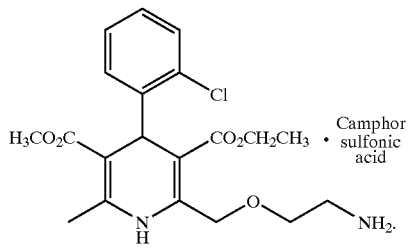

2. A method for preparing amlodipine camsylate of claim 1 which comprises the steps:
   1) dissolving amlodipine of formula (2) in an organic solvent;
   2) adding a camphor sulfonic acid solution in an organic solvent to the amlodipine solution and agitating the mixture for a period sufficient to form a solid;
   3) filtering, washing and drying the solid.

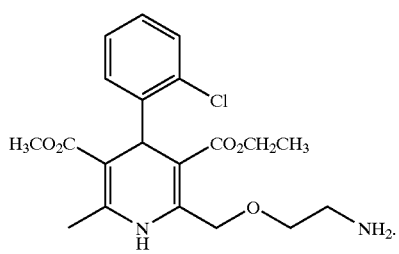

3. The method of claim 2, wherein the camphor sulfonic acid is selected from the group consisting of (1S)-(+)-10-camphor sulfonic acid of formula (3), (1R)-(−)-10-camphor sulfonic acid of formula (4) and racemic 10-camphor sulfonic acid.

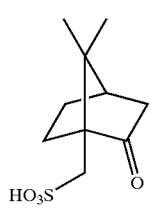

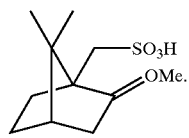

4. The method of claim 2, wherein the concentration of amlodipine of the mixture used in step 2) is 3 to 60 weight %.

5. The method of claim 2, wherein the camphor sulfonic acid is used in a 0.1 to 5.0 equivalent amount based on the amount of amlodipine.

6. The method of claim 2, wherein the organic solvent used in step 1) or 2) is selected from the group consisting of methanol, ethanol, isopropanol and acetonitrile.

7. The method of claim 2, wherein the solid is formed at −10 to 50° C.

8. A pharmaceutical composition comprising the amlodipine camsylate of claim 1 as an effective ingredient and a pharmaceutically acceptable carrier.

* * * * *